(12) United States Patent
Ubukata et al.

(10) Patent No.: US 7,692,778 B2
(45) Date of Patent: Apr. 6, 2010

(54) TRANSFER/INSPECTION APPARATUS AND TRANSFER APPARATUS

(75) Inventors: Tamaya Ubukata, Kawachi-gun (JP); Fow-lai Poh, Kawachi-gun (JP); Masahiro Yaguchi, Kawachi-gun (JP)

(73) Assignee: Tsukuba Seiko Ltd., Mooka-shi (JP)

(*) Notice: Subject to any disclaimer, the term of this patent is extended or adjusted under 35 U.S.C. 154(b) by 262 days.

(21) Appl. No.: 11/660,866

(22) PCT Filed: Aug. 27, 2004

(86) PCT No.: PCT/JP2004/012362

§ 371 (c)(1),
(2), (4) Date: Jul. 27, 2007

(87) PCT Pub. No.: WO2006/022014

PCT Pub. Date: Mar. 2, 2006

(65) Prior Publication Data

US 2007/0273875 A1 Nov. 29, 2007

(51) Int. Cl.
*G01N 21/00* (2006.01)

(52) U.S. Cl. ............... 356/237.2; 117/901; 117/203; 117/201; 310/309

(58) Field of Classification Search ... 356/237.2–237.5, 356/436, 429–430, 239.1; 310/309; 117/201, 117/203, 901
See application file for complete search history.

(56) References Cited

U.S. PATENT DOCUMENTS

| | | | |
|---|---|---|---|
| 4,492,477 A * | 1/1985 | Leser | 356/430 |
| 5,642,198 A * | 6/1997 | Long | 356/430 |
| 5,789,843 A * | 8/1998 | Higuchi et al. | 310/309 |
| 6,359,686 B1 | 3/2002 | Ariglio et al. | |
| 6,683,695 B1 * | 1/2004 | Simpson et al. | 356/632 |
| 6,781,669 B2 * | 8/2004 | Tanaka | 355/53 |
| 7,215,418 B2 * | 5/2007 | Gahagan et al. | 356/237.2 |

FOREIGN PATENT DOCUMENTS

| | | |
|---|---|---|
| JP | A 06-242024 | 9/1994 |
| JP | A 09-322564 | 12/1997 |
| JP | A 2001-41905 | 2/2001 |
| JP | A 2001-198759 | 7/2001 |
| JP | A 2002-39946 | 2/2002 |

* cited by examiner

*Primary Examiner*—Tarifur R. Chowdhury
*Assistant Examiner*—Isiaka O Akanbi
(74) *Attorney, Agent, or Firm*—Oliff & Berridge, PLC (57) ABSTRACT

The invention is to provide a transfer/inspection apparatus capable of inspecting any defect even during transferring and to provide a transfer/inspection apparatus capable of inspecting any defect in a non-contact state during transferring, even if the an object to be transferred is a transparent material. The transfer/inspection apparatus includes a transfer apparatus 2, and a defect inspector 3. The transfer apparatus 2 transfers a thin member 5 in a non-contacted state under control of voltage to be applied to an electrode face, and the defect inspector inspects any defect of the thin member during transferring the thin member. The transfer apparatus 2 is preferably provided with a light beam-transmitting portion (omitted portion 15) at a part of the electrode face for allowing the light beam therethrough. When the defect inspector 3 is arranged by utilizing the light beam-transmitting portion 15, the defect can be inspected in the non-contact manner during transferring, even if the object to be transferred is the transparent material.

12 Claims, 7 Drawing Sheets

TRANSFER/INSPECTION APPARATUS AND TRANSFER APPARATUS

TECHNICAL FIELD

The present invention relates to a transfer/inspection apparatus configured to inspect any defect of a thin member while transferring it in a non-contact state and in addition a transfer apparatus used therefor.

BACKGROUND ART

As a transfer apparatus for assuredly transferring a thin material such as glass, a glass vertical transfer apparatus employing a driving roller system with plural rows of rollers has been practically used, for example (For example, a glass vertical transfer apparatus manufactured by Nippon Setsubi Industries, Ltd.).

However, in case of thin film transistors (TFTs), liquid crystal displays (LCDs), plasma display panels (PDPs), glass substrates, etc. as members to be transferred, transfer apparatuses giving as small impact or contact upon opponent members as possible are desired.

Under the circumstances, an electrostatic holding apparatus which electrostatically holds a thin member in a non-contact state has been proposed (For example, see Patent Document 1). This electrostatic floating transfer apparatus, which is based on an electrostatic floating system using electrostatic force, comprises a stationary part in which an electrode pattern of a conductor is formed on an insulating substrate, an object to be handled which is opposed to and held by the stationary part in a non-contact manner, a proximity switch for detecting a gap between the stationary part and the object, an electric power source for supplying a DC voltage, and a switching circuit for switchingly applying voltage upon electrodes of the stationary part, wherein the DC voltage from the electric power source is switchingly applied to the electrode pattern of the stationary part through the switching circuit based on on/off signals from the proximity switch, so as to stably float the object to be handled.

There is also proposed a thin member handling method and a thin member handling apparatus in which a thin member as an object to be handled is transferred in an inclined state by using the above electrostatic holding apparatus (See Patent Document 2, for example).

Patent Document 2 describes the handling apparatus in which a belt conveyor is provided to support one side edge of the thin member such as the glass sheet or the like, and the thin member is transferred, while the thin member is being held in an inclined state by supporting the above one side edge with the belt conveyor and sucking a face of the thin member with the electrostatic holding apparatus in a non-contact state.

Patent Document 1: JP-H09-322564A
Patent Document 2: JP-2001-198759A

Problems to be Solved

According to the handling apparatus disclosed in Patent Document 2, since the thin material as the object to be handled can be transferred in a state that the thin material is in a substantially non-contact state, this apparatus is suitable for transfer at an improved cleanness degree. Also, since the handling apparatus disclosed in Patent Document 2 can vertically transfer the object (transferring in the inclined state), this apparatus is suitable for a case where large-scale glass material is transferred at a smaller placed area.

As to the glass material as the object to be handled, it is preferable to inspect it with a camera in a proper step inside an actual factory as to whether there is a foreign matter or not. For this purpose, it is preferable that the transfer apparatus can inspect any defect simultaneously and in parallel by utilizing the transferring time period.

However, the handling apparatus disclosed in Patent Document 2 cannot inspect any defect during handling.

If the handling apparatus disclosed in Patent Document 2 is merely configured to be provided with a defect inspector, it may be difficult to inspect any defect with a camera such as a line sensor through image data processing when the object to be handled is transparent.

This is because any defect cannot be inspected at a sufficiently good accuracy. That is, since a spaced distance between the surface of the electrode as the holder and the thin member is as extremely narrow as not more than a few hundreds μm or less, the surface of the electrode located at a back face of the object to be handled is taken as a background into an image taken by the camera even in the state that the holder is in no contact with the object to be handled, if the object is made of a transparent material. Consequently, this causes a noise, which hinders the inspection of the defect at a sufficiently good accuracy.

DISCLOSURE OF THE INVENTION

Therefore, it is a first purpose of the present invention to provide a transfer/inspection apparatus which can inspect any defect of an object during transferring. Further, it is another purpose of the present invention to provide a transfer/inspection apparatus which can perform inspection of any defect of an object in a non-contact state during transferring, even if the object is made of a transparent material.

The present inventors discovered that the transfer/inspection apparatus capable of performing the inspection of defect during transferring can be obtained by equipping a transfer apparatus, which transfers the thin member in a non-contact state under control of voltage to be applied to the face of the electrode, with a defect inspector configured to inspect any defect of the thin member during the transferring. Further, the inventors discovered that the transfer/inspection apparatus which can perform the inspection of any defect of the object during being transferred in a non-contact state, even if the object to be transferred is made of a transparent material, can be obtained by arranging a light beam-transmitting section in a part of a face of an electrode constituting the transfer apparatus and arranging the defect inspector by utilizing the light beam-transmitting section.

That is, the present invention is directed to the transfer/inspection apparatus comprising a transfer apparatus configured to transfer a thin member in a non-contact state under control of voltage to be applied to the face of the electrode, and a defect inspector configured to inspect any defect of the thin member during the transferring.

By employing the above construction, the thin member can be transferred in the non-contact state, while any defect is being inspected.

According to the present invention, it is preferable that a light beam-transmitting section is arranged in a part of the electrode face, and the defect inspector is arranged by utilizing the light beam-transmitting section.

By thus constructing, since the defect inspector is arranged by utilizing the light beam-transmitting section, the surface of the electrode which will cause noise is not taken as a background into an image taken for inspection by the camera even if the object is made of a transparent material. Consequently, any defect can be inspected at a good accuracy during the transferring.

Further, the present invention is to provide a transfer apparatus which is configured to transfer a thin member in a non-contact state under control of voltage to be applied to a face of an electrode and in which a light beam-transmitting section is provided in a part of the face of the electrode.

By so constructing, according to this transfer apparatus, since the defect inspector is arranged by utilizing the light beam-transmitting section, the transfer apparatus can be used for the transfer/inspection apparatus in which the surface of the electrode which will cause noise is not taken as a background into an image taken for inspection by the camera even if the object is made of a transparent material. Consequently, the transfer/inspection apparatus which can inspect any defect at a good accuracy during the transferring can be provided.

The electrode face for supporting the thin member may be constituted by arranging a number of electrode units each having a small electrode surface area and being adjacent to one another in plane. When the above light beam-transmitting section is formed as an omitted portion defined by omitting one or more electrode units, the construction of the transfer/inspection apparatus can be simplified. Further, if the light beam-transmitting section is an omitted portion, noise will not be generated against the image taken for inspection owing to deterioration, change in color, contamination or attachment of dust, etc. of the light beam-transmitting section even if it is used for a long period of time.

When these numerous electrode units are each provided with a control mechanism for controlling a distance between the thin member independently of the other, the inexpensive transfer/inspection apparatus can be provided, even if the object to be handed is flexible or readily broken. For example, the thin member, which is flexible or may be readily broken, can be stably and gently transferred and inspected by decreasing the area of the electrode units and increasing the number thereof, for example. Further, the cost of the entire apparatus can be reduced by increasing the area of the electrode units and decreasing the number thereof. The controller for controlling the space between each of the electrode units and the thin member independent of the other can be configured such that a sensor is provided corresponding to each of the electrode units so that the voltage to be applied to each of the electrode units is controlled to adjust the above space.

As the defect inspector, a line-sensing camera or an area-sensing camera is recited by way of example.

If the defect inspector is the area-sensing camera, the transfer apparatus is provided with a transfer mechanism configured for intermittently transferring the thin member, and the area sensor camera is operated to take in the images necessary for inspection when the transfer mechanism is in a stopped state. In such a construction, even if the thin member as the object to be handled is positionally changed in a thickness direction thereof, the image can be taken in within the focal depth in the state that the thin member is not moved in the planar direction. Consequently, any defect can be inspected at a high accuracy without affording any adverse effect upon the accuracy of taking in the image.

If the defect inspector is further provided with a camera moving unit so that the area sensor camera may be moved by the camera moving unit in a planar direction parallel to the electrode face and in a direction crossing the transferring direction, the thin member having a large width can be inspected by moving the area sensor camera in the direction of crossing the transferring direction without increasing the number of the cameras, even if the camera has a narrow viewing field.

BEST MODE FOR CARRYING OUT THE INVENTION

In the following, specific embodiments of the present invention will be explained with reference to drawings.

Figure 1:
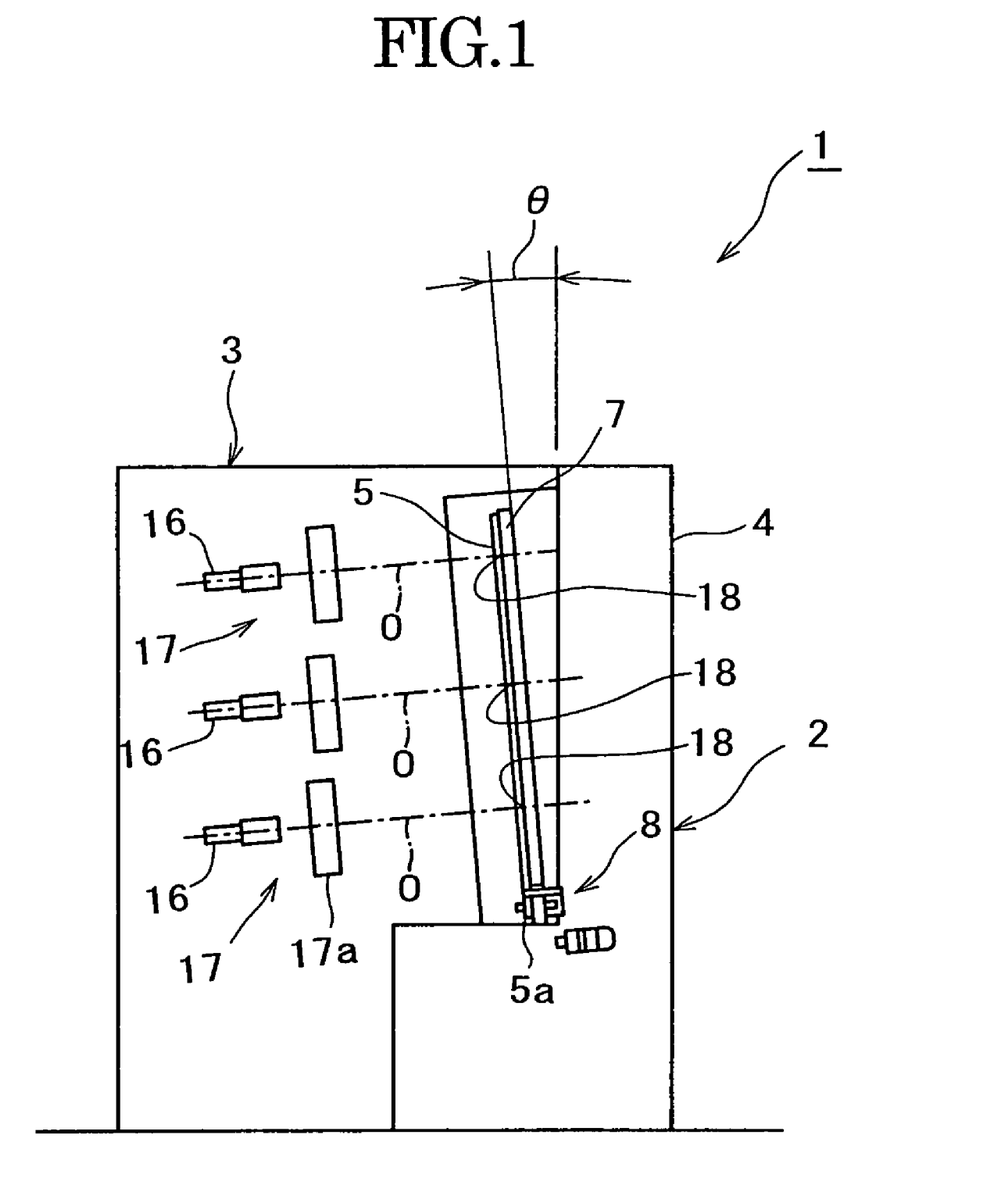
FIG. 1 is a side view for illustrating the construction of the transfer/inspection apparatus according to an embodiment of the present invention.
Figure 2:
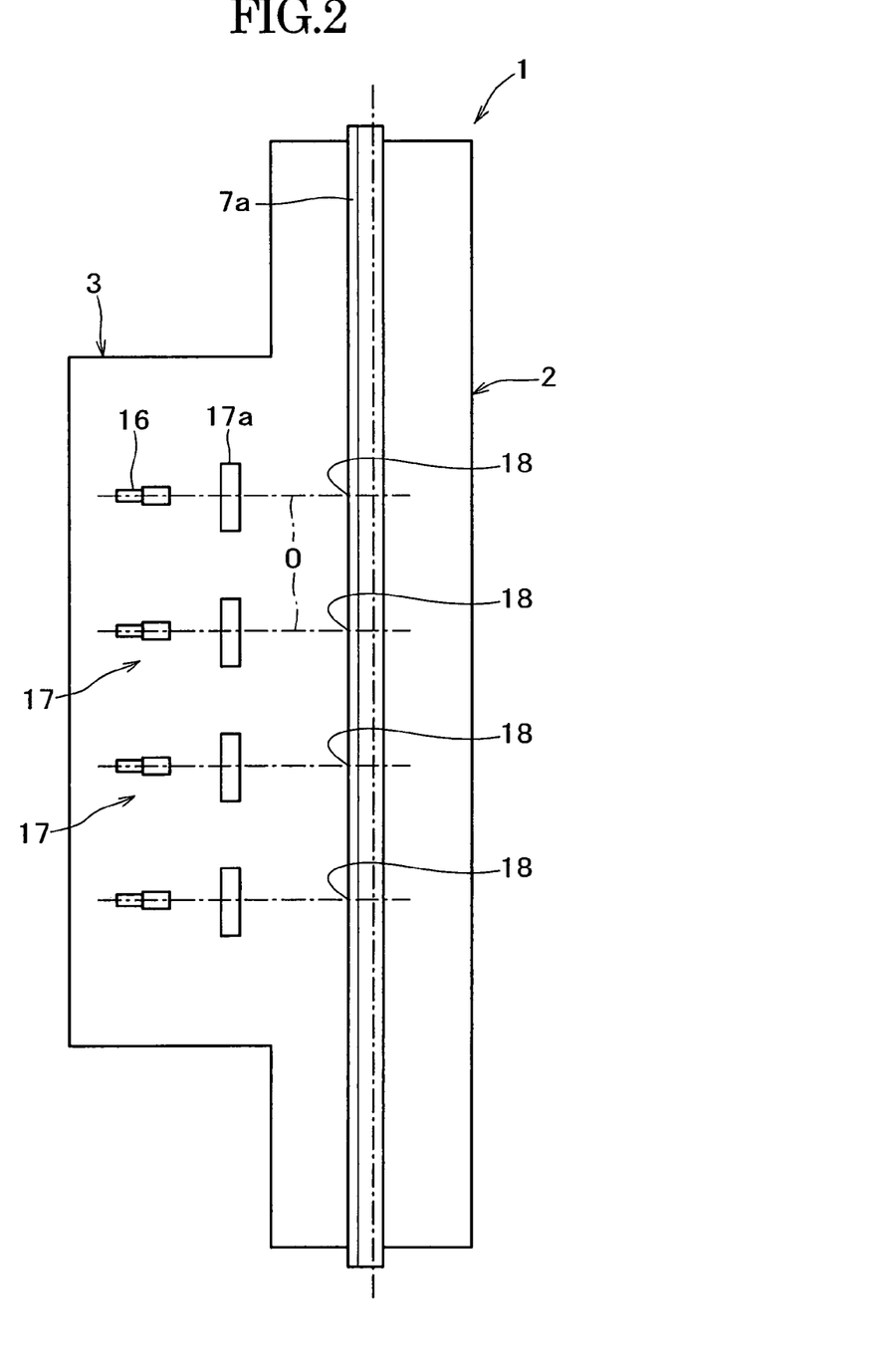
FIG. 2 is a figure for illustrating the relationship between image pickup units 17 and a vertical transfer apparatus 2 of the transfer/inspection apparatus in FIG. 1.

FIGS. 1 and 2 are figures for illustrating the construction of the transfer/inspection apparatus 1 according to the present invention, which apparatus comprises a vertical transfer apparatus 2 and a defect inspector 3.

The vertical transfer apparatus 2 comprises an electrode base 7 (stationary part) and a transfer apparatus 8 such as a belt conveyor. The electrode base 7 comprises an electrode face adapted for electrostatically attracting an object 5 to be handled. The transfer apparatus 8 is arranged under the electrode base 7, and transfers the object 5 while a lower side edge 5a of the object 5 is supported in such a state that the object is electrostatically held relative to the electrode face in a non-contact state (for example, being attracted toward the electrode face while spaced therefrom at a given distance). The electrode base 7 is fixed to an electrode body 4, while an inclination "θ" is freely adjustable relative to the vertical direction (longitudinal direction).

Figure 3:
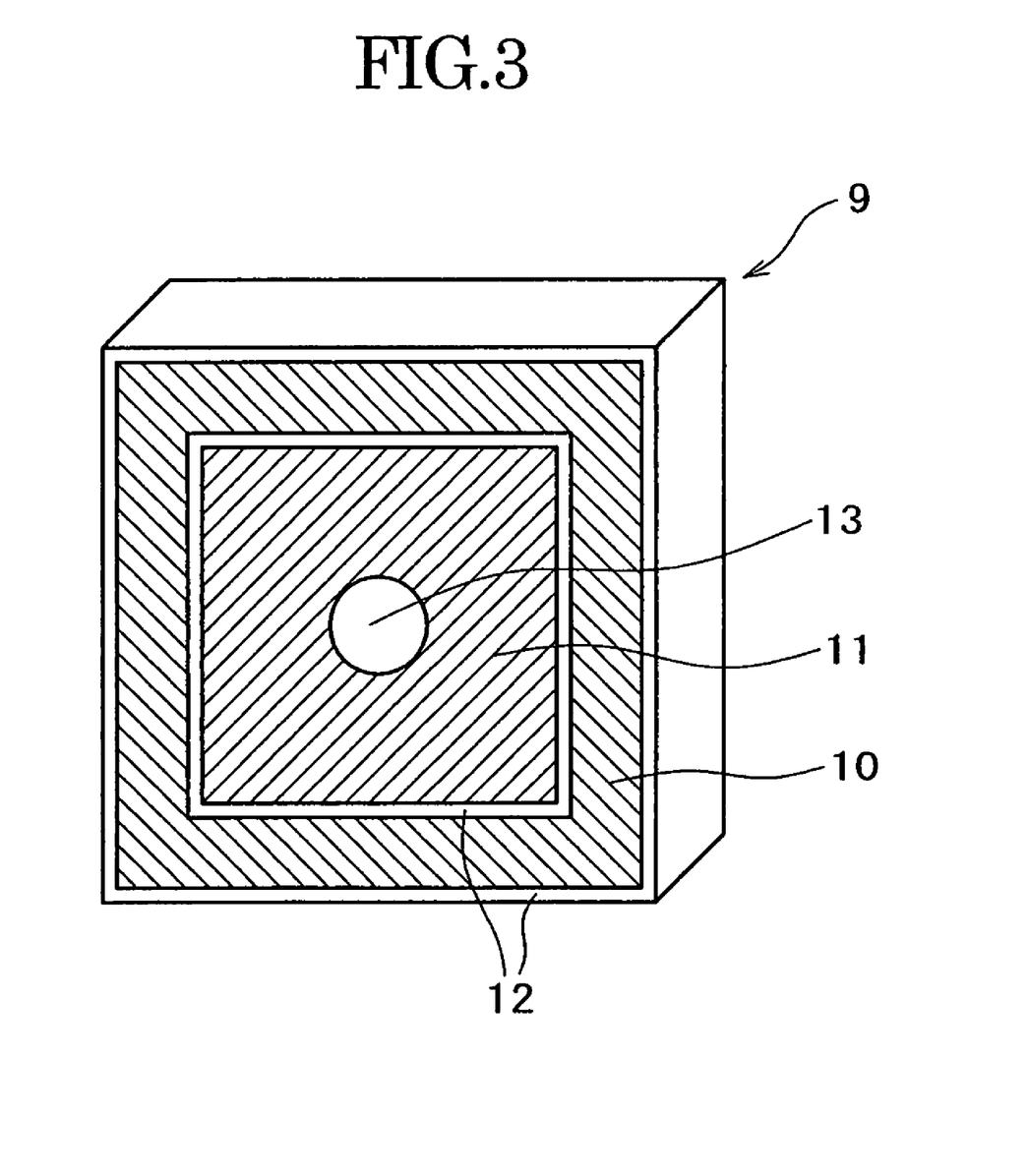
FIG. 3 is a perspective view for illustrating an example of an electrode unit 9 to constitute an electrode base 7 according to an embodiment of the present invention.

The electrode base 7 is constituted by electrode units 9 as shown in FIG. 3 by way of an example of this embodiment of the present invention. In this embodiment, the electrode unit 9 is in a square shape, for example, with an area of 100×100 or 200×200 (unit: mm) as viewed in plane, but is never limited to them. For example, the size is arbitrary, and the shape is not limited to the square. For example, the shape may be round, hexagonal or the like as viewed in plane.

The area of the electrode unit 9 may be determined depending upon the rigidity of the object 5 to be handled. The lower the rigidity of the object 5, preferably the more finely is the area of the electrode unit 9 divided into sections, so that the electrostatically attracting force over the object 5 to be handled is divided into numerous portions to be applied to various portions of the object 5 and the thus divided numerous electrostatically attracting force portions are controlled. The object 5 can be gently and stably handled, when the number of the electrode units 9 is increased, electrodes 10 and 11 for each of the electrode units are designed in an independently dispersion-controllable manner, and the number of proximity switches (the number of the switches, inversion elements, etc. inside a control circuit) is increased in proportion to that of the electrode units 9.

Each of the electrode units 9 is provided with a pair of the electrodes 10 and 11 formed at its face (electrode face) in a pattern shape to afford electrostatic power upon the object 5, and voltages having mutually opposed polarities are applied to the electrodes 10 and 11, respectively from a voltage circuit (not shown).

In this embodiment of the present invention, in order to maintain the potential of the object 5 at a potential of 0 V, an insulating band 12 made of an insulating material is provided between the inner electrode 10 and the outer electrode 11, and the area of the electrode 10 is set equal to that of the electrode 11.

A sensor such as the proximity switch 13, for example is arranged in a central portion inside the electrode 11 to detect the location of the object 5 to be handled. The proximity switch 13 has a switching function (switching circuit for performing switching of the voltage to be applied to each of the electrodes 10 and 11) to switchingly apply voltage to the electrodes 10 and 11 depending upon the spaced distance between the object 5 and the proximity switch 13.

Figure 4:
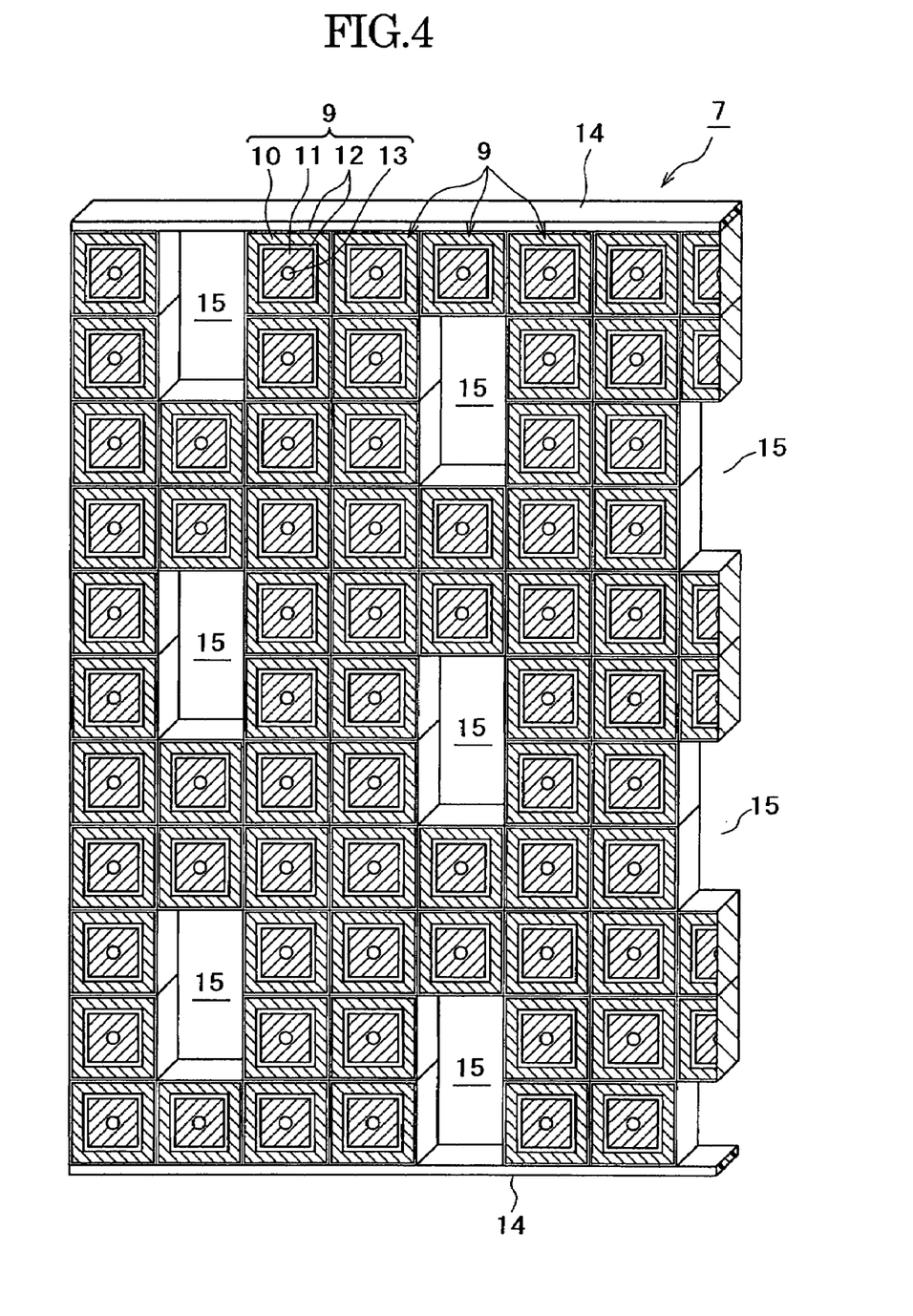
FIG. 4 is a perspective view for illustrating the construction of the electrode base 7 according to the embodiment of the present invention.
Figure 5:
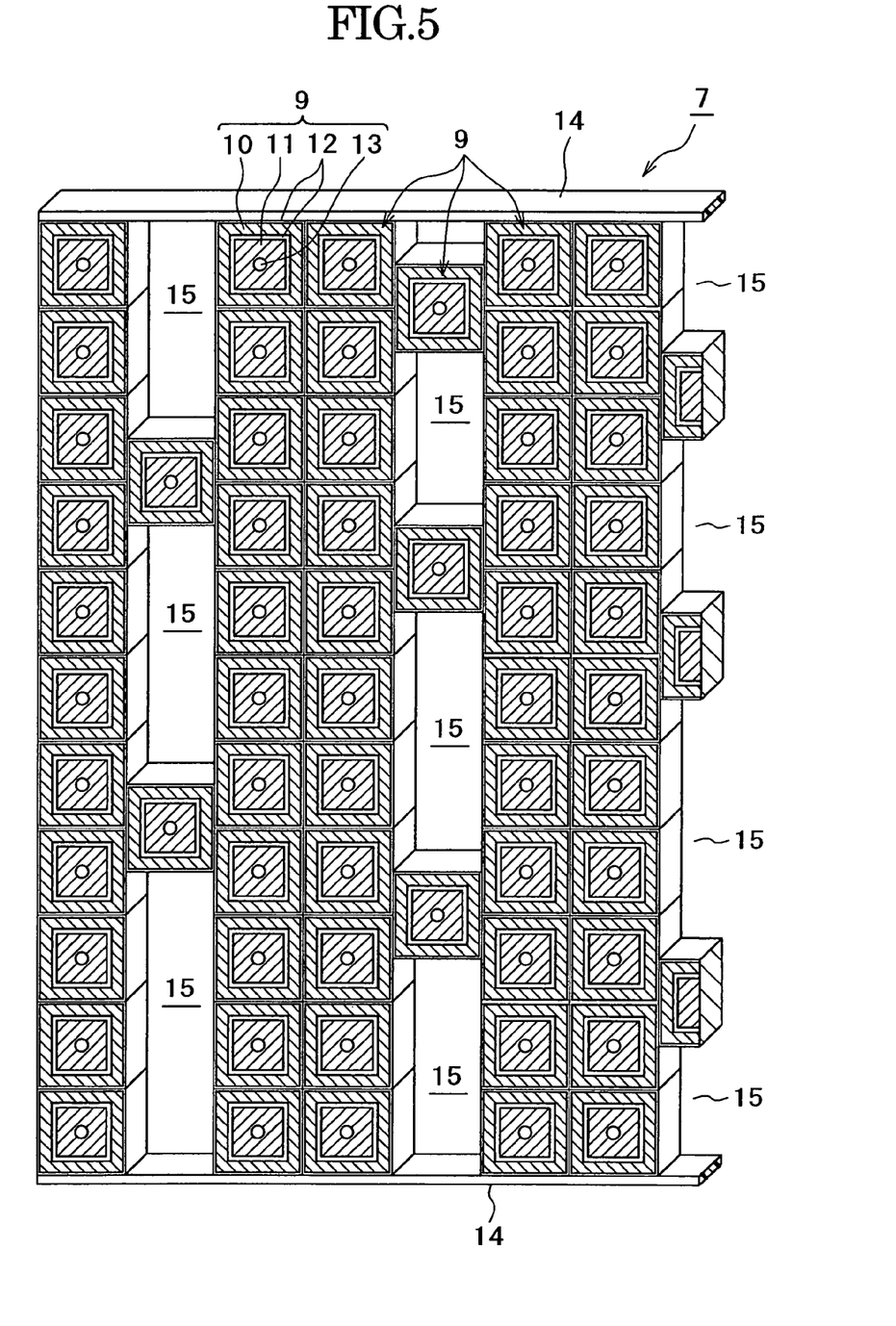
FIG. 5 is a perspective view of a part of a modified construction of the electrode base 7 according to a further embodiment of the present invention.

In this embodiment of the present invention, as shown in FIGS. 4 and 5, a number of the electrode units 9, - - - are arranged in the plane comprising the electrode base 7 in a state that the electrode units are supported by a support (not shown) including a frame body 14. There are provided with omitted portions 15, in a checkered pattern, in a part of the electrode units. The omitted portions 15, which are spaces where no electrode units 9 are arranged, constitute a light beam-transmitting section.

The defect inspector 3 comprises a number of inspection units 17, - - - each equipped with a camera 16 (for example, 2D-CCD camera or area sensor) as an image pickup device. Each of the inspection units 17 comprises at least the pickup unit (camera 16) for taking an image of the object 5. In this embodiment, illumination devices 17a such as ring-shaped illumination are provided for illuminating surfaces of inspection sites of the object 5. The optical axis O, - - - of each of the inspection units 17 is aligned to be at right angle to the surface of the object 5. An optical member may be interposed between the inspection device and the object to diffuse illuminated light, adjust the intensity of the illumination light, or applying a desired wavelength of the illumination light.

Figure 6:
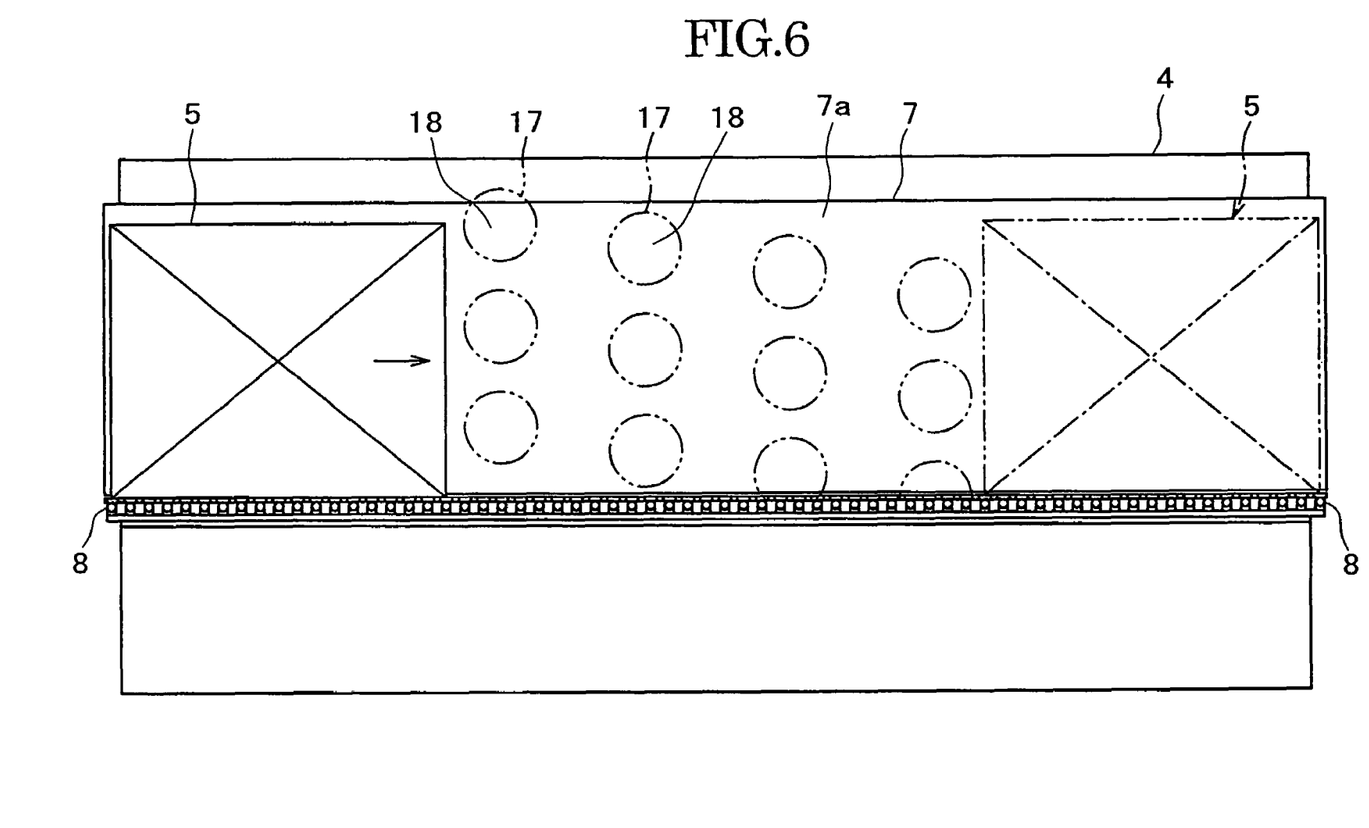
FIG. 6 is a perspective view for illustrating the positional relationship between the transfer apparatus 2 and the image pickup units 17 in the transfer/inspection apparatus according to the embodiment of the present invention as viewed from a front side.

Anyway, the inspection unit 17 is required to be arranged by utilizing the omitted portions 15. In this connection, the wording "by utilizing the omitted portions 15" means that when the camera 16 as in this embodiment takes an image of the object 5 from the front surface side, the omitted portion 15 is located at a rear face of the inspection site. For example, the inspection units 17 are arranged as shown in FIG. 6. By so arranging, the electrode base 7 is not taken as a background into the image taken by the camera 16.

According to the thus constructed defect inspector 3, the application of the DC voltage to the electrodes 10 and 11 of the electrode unit 9 from the electric power source is switched in a pattern fashion through the switching circuit based on on/off signals from the proximity switch 13 in the state that the lower end edge 5a of the object 5 as a transparent material to be handled is placed on the transfer apparatus 8. Thereby, the object 5 can be held in a non-contact manner, while the distance between the object 5 and the proximity switch 13 (electrode face) is maintained at a predetermined target value (for example, a predetermined target value in a range of 300 μm to 500 μm).

Herein, the object 5 to be handled is a transparent glass sheet with a thickness of 0.7 mm, a width of 1500 mm and a length of 1800 mm, for example. The object 5 is handled under control of voltage to be applied so that the clearance is at a given value in a range of 300 μm to 500 μm in the state that the object is supported at the lower end edge 5a on the transfer apparatus 8 in an almost vertical state of θ=5°.

When the transfer apparatus 8 is driven in this state, the object to be handled can be moved in a direction of an arrow.

Then, when an inspection site of the object 5 comes to an image pickup range of the camera 16, the transfer apparatus 8 is stopped and an image is taken in by the camera 16. By so doing, the image taken in is transmitted to an appropriate image processing unit (not shown) where it is judged whether a foreign mark or matter such as scratch, crack, bubble, hole, side mark or the like is present or not. The background will not form a noise in the thus taken image even if the object 5 is transparent, since the omitted portion 15 is arranged at the rear face of the object 5.

Although the object 5 wiggles in the thickness direction during taking the image, the wiggling causes no noise if this wiggle is within the focal depth range of the camera 16, since the optical axis O of the camera 16 crosses the object 5 at right angle.

After the image is taken in, the transfer apparatus moves the object 5 at a distance corresponding to the viewing field of the camera and stops it. Then, a next image is picked up. By this, the defect inspector can inspect any defect at a high accuracy without noise.

Modified Embodiments

Figure 7:
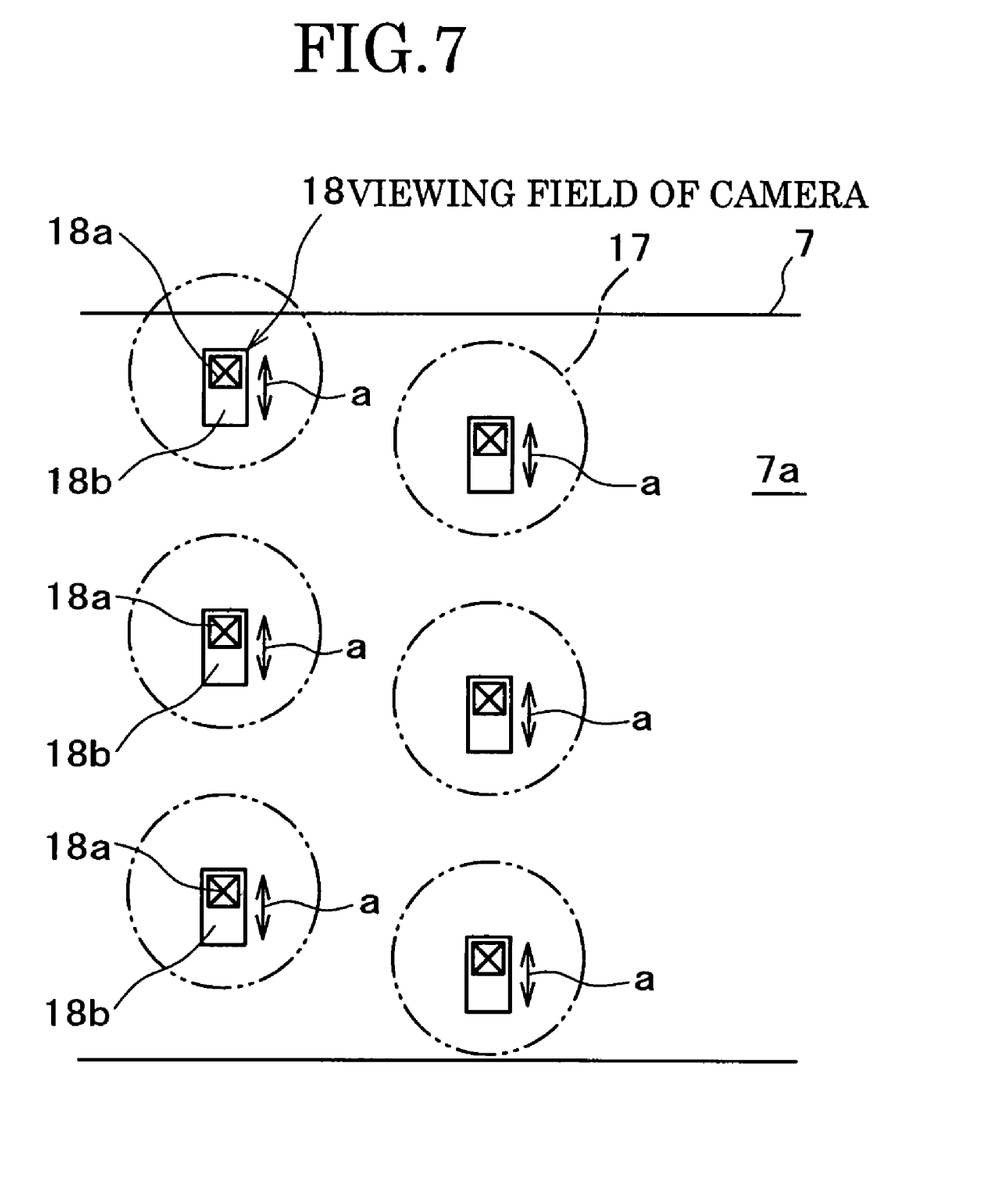
FIG. 7 is a view of illustrating moving directions of image pickup devices in the image pickup units 17 of a modified example of the transfer/inspection apparatus.

As shown in FIG. 7, this modified embodiment is the same as the above one except that the camera 16 of the inspection unit 17 is moved in parallel to the surface of the object 5 to be handled and in a direction "a" crossing the transfer direction (for example, at right angle).

By so constructing, after the image within the viewing field 18a of the camera is taken in, the camera is moved to a viewing field 18b in the direction "a" and takes in an image. After the images are taken in with respect to the viewing fields 18a and 18b, the transfer apparatus 8 is driven to move the glass by a distance corresponding to the width of the viewing field of the camera, followed by picking up a next image.

Thus, even if the viewing field of camera is narrow, the object 5 having a large width can be inspected without increasing the number of the cameras.

Although the embodiments of the present invention have been explained in detail with reference to the drawings, the present invention is not limited to the specific constructions of these embodiments. Any changes, modifications or the like fall in the scope of the invention without departing from the gist of the present invention.

Explanation has been made of the case where the object 5 to be handled is spaced in parallel to the electrode base 7 with respect to the relatively positional relationship between the object 5 and the electrode base 7, the object 5 may be inclined relative to the electrode base 7, for example. For example, although the lower end edge 5a approaches the electrode base 7 in the above embodiments of the present invention, the distance between the object and the electrode base becomes larger as the location goes upwardly. That is, the object may be held while the distance between the object and the electrode base becomes wider as the location goes upwardly.

In addition, although the illuminating device 17a illuminates the object 5 from the front surface side thereof, the object may be illuminated from the back face side. In this case, the illumination devices 17a are arranged by utilizing the omitted portions 15.

Although an image of the object 5 is picked up by the defect inspector 3, this image may be picked up from the back face side of the object 5 by utilizing the omitted portion 15. In this case, the illuminating device 17a may illuminate the body from either the front surface side or the back surface side.

In the above embodiments of the present invention, the proximity switch 13 is used. A displacement sensor may be used instead of the switch 13. It may be that the gap between the electrode face and the object 5 is sensed by the displacement sensor, signals are transmitted to the controller or the like, the controller controls the voltage to be applied to each of the electrode units in accordance with the gap, and the gap is maintained to the predetermined value. An on/off controller is most inexpensive as the system of controlling the voltage to be applied.

Although the area sensor is used as the defect inspector in the above-mentioned embodiments, a line sensor or the like may be used. In this case, the vertical type transfer apparatus 8 may be intermittently or continuously transferred.

Although the vertical type transfer apparatus 8 is explained as the transfer apparatus by way of example, the transfer apparatus is not limited to the vertical type if the installation space is acceptable.

Although the light-beam-transmitting section is formed as the omitted portion in the above embodiment of the present invention, it may be formed by a transparent material as long as it permits a light beam.

Although the transfer apparatus and the inspection apparatus are integrally formed in the above embodiments of the present invention, they may be separately produced. For example, the transfer apparatus may be provided with a fitting portion for the camera which can be arranged after located corresponding to the light beam-transmitting section. The transfer/inspection apparatus according to the present invention can be provided by fitting a commercially available inspection camera to the fitting section.

INDUSTRIAL APPLICABLE FIELD

As mentioned above, the present invention provides the transfer/inspection apparatus which can inspect the object to be transferred, such as LCD, PDP, a glass substrate or the like during transferring in a non-contact manner. Thus, the invention has the industrially variable effect that the invention can provide a transfer/inspection apparatus which can inspect any defect of an object in a non-contact manner during transferring, even if the object is made of a transparent material.

What is claimed is:
1. A transfer/inspection apparatus, comprising:
a transfer apparatus having an electrode face and configured to transfer a thin member in a non-contacted state under control of voltage to be applied to the electrode face;
a defect inspector configured to inspect the thin member during transferring the thin member; and
a light beam-transmitting portion provided at a part of the electrode face, wherein
the defect inspector is arranged by utilizing the light beam-transmitting portion,
the electrode face comprises a number of electrode units each having a small-area electrode face and arranged adjacent to one another in a planar manner, and
the light beam-transmitting portion is formed in the form of a missing portion formed by omitting one or plural electrode units.

2. The transfer/inspection apparatus set forth in claim 1, wherein
a number of the electrode units each comprise a control mechanism for independently controlling a space between the electrode unit and the thin member.

3. The transfer/inspection apparatus set forth in claim 2, wherein the defect inspector is a line-sensing camera or an area-sensing camera.

4. The transfer/inspection apparatus set forth in claim 2, wherein
the defect inspector is an area-sensing camera,
the transfer apparatus comprises a transfer mechanism for intermittently transferring the thin member and
an image necessary for the inspection is taken in by operating the area sensing camera in a state that the transfer mechanism is in a stopped state.

5. The transfer/inspection apparatus claimed in claim 4, wherein
the defect inspector further comprises a camera-moving device, and the area-sensing camera is moved in a planar direction parallel to the electrode face and in a direction crossing the transferring direction.

6. The transfer/inspection apparatus claimed in claim 4, wherein
a focal depth of the area-sensing camera meets a fluctuating area of the thin member in a thickness direction thereof in a state that the thin member is held electrostatically in addition to the thickness of the thin member.

7. The transfer/inspection apparatus set forth in claim 1, wherein
the defect inspector is a line-sensing camera or an area-sensing camera.

8. The transfer/inspection apparatus set forth in claim 1, wherein
the defect inspector is an area-sensing camera,
the transfer apparatus comprises a transfer mechanism for intermittently transferring the thin member, and
an image necessary for the inspection is taken in by operating the area sensing camera in a state that the transfer mechanism is in a stopped state.

9. The transfer/inspection apparatus claimed in claim 8, wherein
the defect inspector further comprises a camera-moving device, and the area-sensing camera is moved in a planar direction parallel to the electrode face and in a direction crossing the transferring direction.

10. The transfer/inspection apparatus claimed in claim 8, wherein
a focal depth of the area-sensing camera meets a fluctuating area of the thin member in a thickness direction thereof in a state that the thin member is held electrostatically in addition to the thickness of the thin member.

11. A transfer apparatus configured to transfer a thin member in a non-contact state under control of a voltage to be applied to an electrode face, the transfer apparatus comprising a light beam-transmitting portion provided in a part of said electrode face, wherein
the electrode face comprises a number of electrode units each having a small-area electrode face and arranged adjacent to one another in a planar manner, and the light beam-transmitting portion is formed in the form of a missing portion formed by omitting one or plural electrode units.

12. The transfer apparatus claimed in claim 11, wherein a number of the electrode units each comprise a control mechanism for independently controlling a space between the electrode unit and the thin member independently of the other electrode units.

* * * * *